US006986889B2

United States Patent
Laffer et al.

(10) Patent No.: US 6,986,889 B2
(45) Date of Patent: Jan. 17, 2006

(54) COMPOUND FOR TREATMENT OF ALLERGY AND ASTHMA

(75) Inventors: Sylvia Laffer, Vienna (AT); Erik Högbom, Uppsala (SE); Kenneth H. Roux, Tallahassee, FL (US); Jonas Adriansson, Uppsala (SE); Wolfgang R. Sperr, Vienna (AT); Peter Valent, Vienna (AT); Dietrich Kraft, Vienna (AT); Hans Grönlund, Lidingö (SE); Rudolf Valenta, Vienna (AT)

(73) Assignee: Pharmacia Diagnostics AB, Uppsala (SE)

( * ) Notice: Subject to any disclaimer, the term of this patent is extended or adjusted under 35 U.S.C. 154(b) by 236 days.

(21) Appl. No.: 10/108,301

(22) Filed: Mar. 28, 2002

(65) Prior Publication Data

US 2003/0035796 A1 Feb. 20, 2003

Related U.S. Application Data

(60) Provisional application No. 60/279,109, filed on Mar. 28, 2001.

(30) Foreign Application Priority Data

Mar. 28, 2001 (SE) .............................. 0101093

(51) Int. Cl.
*A61K 39/395* (2006.01)
*C07K 16/00* (2006.01)
*C07K 16/46* (2006.01)
*C12P 21/08* (2006.01)

(52) U.S. Cl. ................ 424/133.1; 424/141.1; 424/142.1; 424/145.1; 424/134.1; 530/387.1; 530/387.3; 530/388.15; 530/388.24

(58) Field of Classification Search .............. 424/133.1, 424/134.1, 141.1, 142.1, 145.1; 530/387.1, 530/387.3, 388.15, 388.24
See application file for complete search history.

(56) References Cited

U.S. PATENT DOCUMENTS

| 5,543,144 A | 8/1996 | Chang |
| 5,625,039 A | 4/1997 | Washida et al. |
| 6,037,453 A | 3/2000 | Jardieu et al. |
| 6,180,370 B1 * | 1/2001 | Queen et al. |

FOREIGN PATENT DOCUMENTS

| WO | 00 63252 | 10/2000 |
| WO | 00 72879 | 12/2000 |

OTHER PUBLICATIONS

Colman et al, 1994, A structural view of immune recognition by antibodies, pp. 33–34.*
Abaza et al, J of Protein Chemistry 11(5): 433–444, 1992.*
Heusser et al, Current Opinion in Immunology 9: 805–814, 1997.*
Harlow et al in Antibodies a Laboratory Manual, 1998, Cold Spring harbor laboratory publication, Cold Spring Harobr, NY, pp. 626–629.*
Rudolf et al, J Immunology 157: 5646–5652, 1996.*
Valenta et al, International archives of allergy and immunology 113(1–3): 258–9, 1997.*
Kuby et al, 1994, Immunology, Second edition, pp. 86–96.*
V. Casolaro et al., "Biology and Genetics of Atopic Disease", *Curr. Opin. Immunol.*, 1996, pp. 796–803, vol. 8.
M.A. Beaven et al., "Signal Transduction by Fc Receptors: The FcεRI Case", *Immunology Today*, 1993, pp. 222–226, vol. 14, No. 5.
G.C. Mudde et al., "Allergen Presentation by Epidermal Langerhans' Cells from Patients with Atopic Dermatitis is Mediated by IgE", *Immunology*, 1990; pp. 335–341, vol. 69.
D. Maurer et al., "The High Affinity IgE Receptor (FcεRI) Mediates IgE–Dependent Allergen Presentation", *Journal of Immunology*, 1995, pp. 6285–6290, vol. 154.
T. Bierber, " FcεRI ON antigen–pRESenting Cells", *Curr. Opin. Immunol.*, 1996, pp. 773–777, vol. 8 .
K. Ishizaka et al., "Identification of äE–Antibodies as a Carrier of Reaginic Activity", *The Journal of Immunology*, 1967, pp. 1187–1198, vol. 99, No. 6.
S.G.O. Johansson et al., "Immunological Studies of an Atypical (Myeloma) Immunoglobulin", *Immunology*, 1967, pp. 381–394, vol. 13.
J.V. Ravetch et al., "Fc Receptors", *Ann. Rev. Immunol.*, 1991, pp. 457–492, vol. 9.
B. Helm et al., "Peptide Blocking of IgE/Receptor Interaction: Possibilities and Pitfalls", *Allergy*, 1997, pp. 1155–1169, vol. 52.
B. Helm et al., "The Mast Cell Binding Site on Human Immunoglobulin E", *Nature*, Jan. 1988, pp. 180–183, vol. 331, No. 14.
B. Helm et al., "Identification of the High Affinity Receptor Binding Region in Human Immunoglobulin E", *The Journal of Biological Chemistry*, 1996, pp. 7494–7500, vol. 271.

(Continued)

*Primary Examiner*—Christina Chan
*Assistant Examiner*—Phuong Huynh
(74) *Attorney, Agent, or Firm*—Browdy and Neimark

(57) ABSTRACT

The present invention relates to a novel drug candidate having a potential for universal therapy of allergy and asthma.

Figure 1:
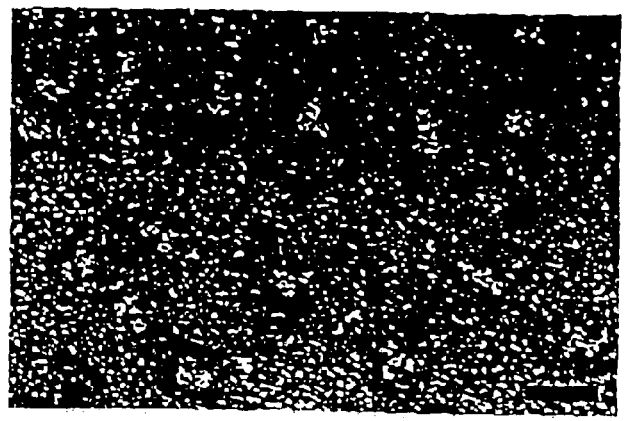
Figure 1:
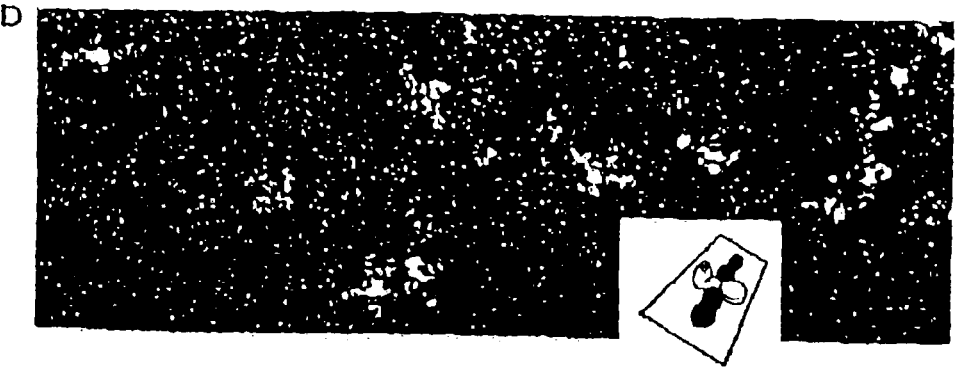
Figure 1:
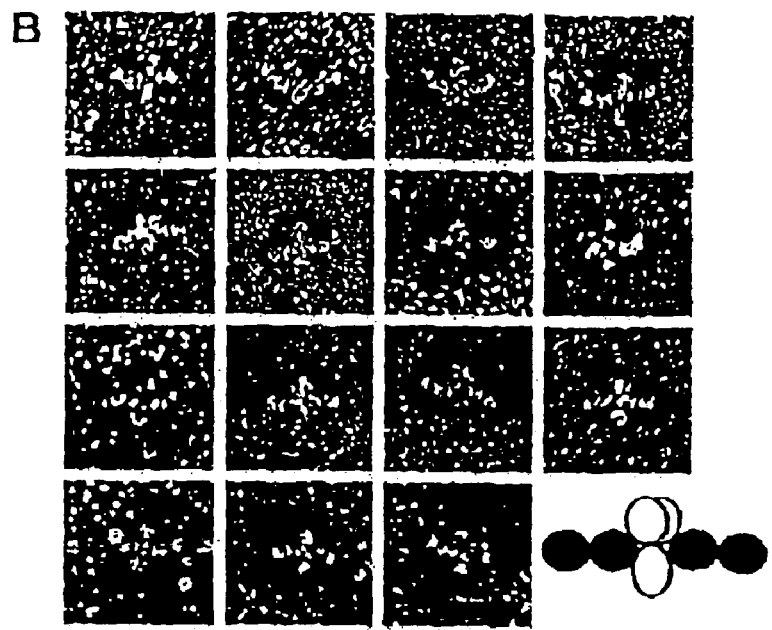
Figure 1:
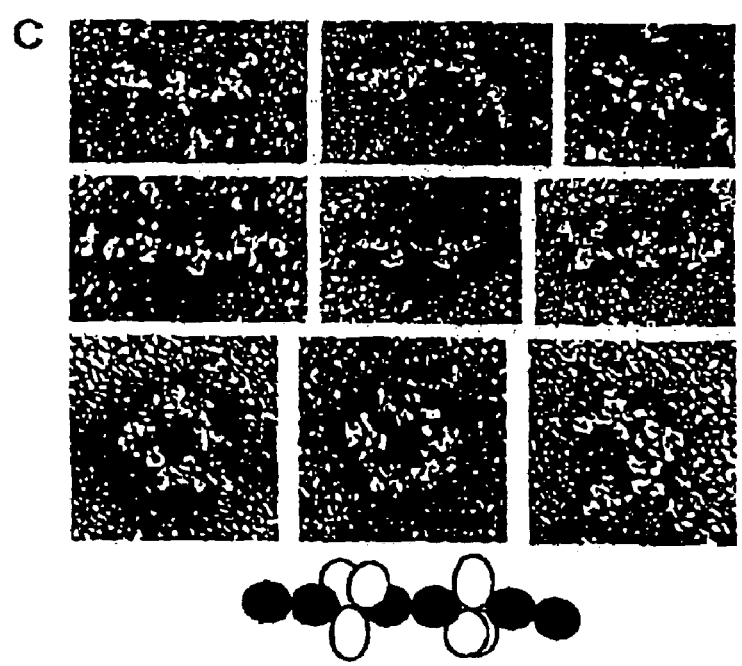

The invention provides a Fab (antibody fragment), having the following characteristics:
a) inhibits the IgE-FcεRI interaction;
b) binds to free and cell-bound IgE; and
c) is non-anaphylactic.

15 Claims, 6 Drawing Sheets

OTHER PUBLICATIONS

A. Nissim et al., "Mapping of the High Affinity Fcå Receptor Binding Site to the Third Constant Region Domain of IgE", *The EMBO Journal*, 1991, pp. 101–107, vol. 10, No. 1.

L. Presta et al., "The Binding Site on Human Immunoglobin E for Its High Affinity Receptor", *The Journal of Biological Chemistry*, 1994, pp. 26368–26373, vol. 269, No. 42.

B. Helm et al., "Blocking of Passive Sensitization of Human Mast Cells and Basophil Granulocytes with IgE Antibodies by a Recombinant Human å–chain Fragment of 76 Amino Acids", *Proc. Natl. Acad. Sci.*, 1989, pp. 9465–9469, vol. 86.

M. Basu et al., "Purification and Characterization of Human Recombinant IgE–Fc Fragments that Bind to the Human High Affinity IgE Receptor", *The Journal of Biological Chemistry*, 1993, pp. 13118–13127, vol. 268, No. 18.

L. Vangelista et al., "The Immunoglobulin–like Modules Cå3 and å2 are the Minimal Units Necessary for Human IgE–FcåRI Interaction", *The Journal of Clinical Investigation*, 1999, pp. 1571–1578, vol. 103, No. 11.

R.N. Hamburger, "Peptide Inhibition of the Prausnitz–Küstner Reaction", *Science*, 1975, pp. 389–390, vol. 189.

J.M. McDonnell et al., "Structure Based Design and Characterization of Peptides that Inhibit IgE Binding to Its High–Affinity Receptor", *Nature Structural Biology*, 1996, pp. 419–426, vol. 3, No. 5.

S.C. Garman et al., "Crystal Structure of the Human High–Affinity IgE Receptor", *Cell*, pp. 951–961, vol. 96.

L. Hellman, "Profound Reduction in Allergen Sensitivity Following Treatment With a Novel Allergy Vaccine", *Eur. J. Immunol.*, 1994, pp. 415–420, vol. 24.

T.W. Wiegand et al., "High–Affinity Oligonucleotide Ligands to Human IgE Inhibit Binding to Fcå Receptor I", *J. Immunol.*, 1996, pp. 221–230, vol. 157.

L.G. Presta et al., "Humanization of an Antibody Directed Against IgE", *The Journal of Immunology*, 1993, pp. 2623–2632, vol. 151, No. 5.

C. Heusser et al., "Therapeutic Potential of Anti–IgE Antibodies", *Curr. Opin. Immunol.*, 1997, pp. 805–813, vol. 9.

S.T. Holgate et al., "Treatment of Allergic Airways Disease with Anti–IgE", *Allergy*, 1998, pp. 83–88, vol. 53.

D.T.W. Fei et al., "A Novel Bioactivity Assay for Monoclonal Antibodies Directed Against IgE", *Journal of Immunological Methods*, 1994, pp. 189–199, vol. 171.

C.H. Heusser et al., "Demonstration of the Therapeutic Potential of Non–Anaphylactogenic Anti–IgE Antibodies in Murine Models of Skin Reaction, Lung Function and Inflammation", *Int. Arch. Allergy Immunol.*, 1997, pp. 231–235, vol. 113.

H. Breiteneder et al., "The Gene Coding for the Major Birch Pollen Allergen Betvi, is Highly Homologous to a Pea Disease Resistance Response Gene", *The EMBO Jounral*, 1989, pp. 1935–1938, vol. 8, No. 7.

S. Laffer et al., "Molecular Characterization of Bip 1, a Monoclonal Antibody that modulates IgE Binding to Birch Pollen Allergen, Bet v $1^{1}$", *J. Immunol.*, 1996, pp. 4953–4962, vol. 157.

K. Hoffman–Sommergruber et al., "High–Level Expression and Purification of the Major Birch Pollen Allergen, Bet v 1", *Protein Expression and Purification*, 1997, pp. 33–39, vol. 9.

P. Wiedemann et al., "Molecular and Structural Analysis of a Continuous Birch Profilin Epitope Defined by a Monoclonal Antibody", *The Jounral of Biological Chemistry*, 1996, pp. 29915–29921, vol. 271, No. 47.

K.H. Roux, "Immunoelectron Microscopy of Idiotype–Anti–Idiotype Complexes", *Meth. Enzymol*, 1989, pp. 130–144, vol. 178.

K.H. Roux, "Negative–Stain Immunoelectron–Microscope Analysis of Small Macromolecules of Immunologic Significance", *Methods: A Companion to Methods in Enzymology*, 1996, pp 247–256, vol. 10.

K.H. Roux et al., "Comparisons of the Ability of Human IgG3 Hinge Mutants, IgM, IgE, and IgA2, to Form Small Immune Complexes: A Role for Flexibility and Geometry", *J. Immunol.*, 1998, pp. 4083–4090, vol. 161.

P. Valent et al., "Mast Cell Typing: Demonstration of a Distinct Hematopoietic Cell Type and Evidence for Immunophenotypic Relationship to Mononuclear Phagocytes", *Blood*, 1989, pp. 1778–1785, vol. 73.

A.L. De Weck et al., "Good or Bad IgE and Anti–IgE Antibodies: New Molecular Concepts", *Molecular Biology and Immunology of Allergens*, Boca Raton, Florida: CRC Press, 1993, pp. 101–112.

M.P Rudolf et al., "Effect of Anti–IgE Antibodies on FceRI–Bound $IgE^{1}$", *J. Immunol.*, 1996, pp. 5646–5652, vol. 157.

M.B. Keown et al., "Hydrodynamic Studies of a Complex Between the Fc Fragment of Human IgE and a Soluble Fragment of the FceRI α Chain", *Proc. Natl. Acad. Sci.*, 1995, pp. 1841–1845, vol. 92.

M.B. Keown et al., "Basis of the 1:1 Stoichiometry of the High Affinity Receptor Fcε RI–IgE Complex", *Eur. Biophys. J.*, 1997, pp. 471–476, vol. 25.

P. Valent et al., "Interleukin 3 Activates Human Blood Basophils Via High–Affinity Binding Sites", *Proc. Natl. Acad. Sci.*, 1989, pp. 5542–5546, vol. 86.

R. Valenta et al., "Induction of Specific Histamine Release from Basophils with Purified Natural and Recombinant Birch Pollen Allergens", *J. Allergy Clin. Immunol.*, 1993, pp. 88–97, vol. 91.

H. Milgrom et al., "Treatment of Allergic Asthma with Monoclonal Anti–IgE Antibody", *The New England Journal of Medicine*, 1999, pp. 1966–1973, vol. 341.

Y.S. Lebedin et al., "Ex Vivo Removal of IgE in Atopic Asthma by Extracorporeal Plasmoimmunoadsorption (EPIA): Development of a Clinical Adsorbent", *Int. J. Artif, Organs*, 1991, pp. 508–514, vol. 14.

Rudolf et al., "Molecular Basis for Nonanaphylactogenicity of a Monoclonal Anit–IgE Antibody" *The Journal of Immunology*, (2000), vol. 165, pp. 813–819.

* cited by examiner

COMPOUND FOR TREATMENT OF ALLERGY AND ASTHMA

The present application claims the benefit of U.S. Provisional Appln. No. 60/279,109, filed Mar. 28, 2001.

FIELD OF THE INVENTION

The present invention relates to a novel compound for treatment of allergy and asthma. More precisely, the invention relates to a novel anti-IgE Fab (antibody fragment) and medical use thereof.

BACKGROUND OF THE INVENTION

Type I allergy represents an immunologically-mediated hypersensitivity disease which affects almost 25% of the population worldwide [1]. Allergic patients suffer from the increased and inappropriate production of IgE antibodies against otherwise harmless antigens (pollen-, mite-, mould-, hair/dander-allergens) [1, 2]. Allergen-mediated crosslinking of IgE antibodies bound to effector cells (e. g., mast calls, basophils) via FcεRI induces the immediate release of biologically active mediators (histamine, leukotrienes) and causes the acute symptoms of atopy (e.g., allergic rhinitis, conjunctivitis, asthma and anaphylactic shock) [3]. When allergens are presented via IgE-FcεRI on professional antigen-presenting cells (e.g., monocytes, dendritic cells), T cells become activated and release Th2 cytokines thus leading to chronic, delayed disease manifestations (atopic dermatitis, chronic asthma) [4–6].

The interaction of allergens, allergen-specific IgE and FcεRI therefore represents a key pathomechanism in atopy and many forms of asthma. Since the identification and characterization of IgE antibodies [7, 8] and FcεRI [9], considerable effort has been spent in the analysis of their interactive domains and in particular to identify competitors of this interaction for a universal therapy of atopic disease [10]. Attempts to determine the interactive sites between human IgE and the alpha chain of FcεRI [11–14] comprised the screening of recombinant proteins/peptides [15–17], mutant proteins [14], chemically synthesized peptides [18, 19], and structural analyses [20]. Furthermore, attempts were made to induce autoantibody responses against the receptor binding site of IgE [21] in order to prevent IgE binding to FcεRI. Other therapeutic approaches comprise the development of IgE-derived peptides [15, 18, 19], nucleic acids [22] and humanized anti-IgE antibodies [23–25]. Most of the described competitors result from laborious structural and rationale design [19] combined with evaluation in sophisticated cellular assays (e.g., basophil histamine release) [26] or from extensive in vivo testing [27]. Although many compounds have been described sofar, there still remains a need of improvements within this area.

SUMMARY OF THE INVENTION

According to the invention a unique compound has been identified, an antibody fragment called Fab 12, which is a novel inhibitor/competitor of the IgE-FcεRI interaction.

Fab12 may represent a candidate molecule for universal therapy of atopy and asthma because it can be used for the depletion of circulating IgE antibodies as well as of IgE-bearing cells. Primarily, Fab 12 is intended for use as a drug for treatment of acute or chronic atopy, especially for treatment of type I allergy and asthma.

In a first aspect, the invention provides an anti-IgE Fab (antibody fragment) of $IgG_1$ isotype, having the following characteristics:

a) inhibits the IgE-FcεRI interaction;

b) binds to free and cell-bound IgE; and c) is non-anaphylactic.

The Fab may be derived from a monoclonal or polyclonal antibody.

Alternatively, the Fab is synthetically or recombinantly produced.

In a preferred embodiment the Fab is a recombinant Fab comprising humanized framwork regions.

The hybridoma cell line producing the Mab 12 and Fab 12 of the invention has been deposited on Mar. 27, 2002, under accession number 02032734 at the European Collection of Cell Cultures (ECACC), Salisbury, Wiltshire, SP4 OJG, UK.

In a second aspect, the invention provides use of a Fab according to the invention for the production of a drug for treatment of atopic conditions. The atopic condition may be an acute or chronic atopic condition. Furthermore, the invention relates to use of said Fab for depleting IgE and IgE bearing cells from the circulation. Preferably, this use is extracorporal.

Another use according to the invention is targeting of IgE bearing cells for therapeutical intervention at the cellular level. The Fab according to the invention is then provided, for example by derivatization, with e.g. a toxin in the purpose of inactivating effector cells, plasma cells (B cells) end/or antigen presenting cells.

DETAILED DESCRIPTION OF THE INVENTION

The invention will now be described more closely in association with an experimental section as well as the accompanying drawings:

FIG. 1 Electron micrographs. Electron micrograph of a field of unreacted chimeric Bip 1 IgE molecules, (a). Electron micrographic gallery and interpretive diagram of IgE in complex with a molar excess (b) or with an equimolar amount of mAb 12 F(ab')$_2$ (c). (d) Shows IgE reacted with a molar excess of mAb12 F(ab')$_2$. An upturned C-terminal region of IgE Fc is indicated by stipples. Arrows indicate regions where the protein is thickest in the Z axis (d). The bars in all Figures correspond to 25 nm. Open figures in the diagrams represent IgE and solid figures mAb12 F(ab)$_2$.

FIG. 2. mAb 12 can desensitize human basophils. Enriched basophils were preincubated with either mAb 12, E-124-2-8/Dε2, a control antibody (co-ab) without reactivity to IgE or with buffer alone. Cells were then exposed to various concentrations of mAb 12 (a) or E-124-2-8/Dε2 (b) (x-axis). The percentages of released histamine in comparison with total histamine are shown on the y-axis. Results represent means of triplicates.

Figure 3:
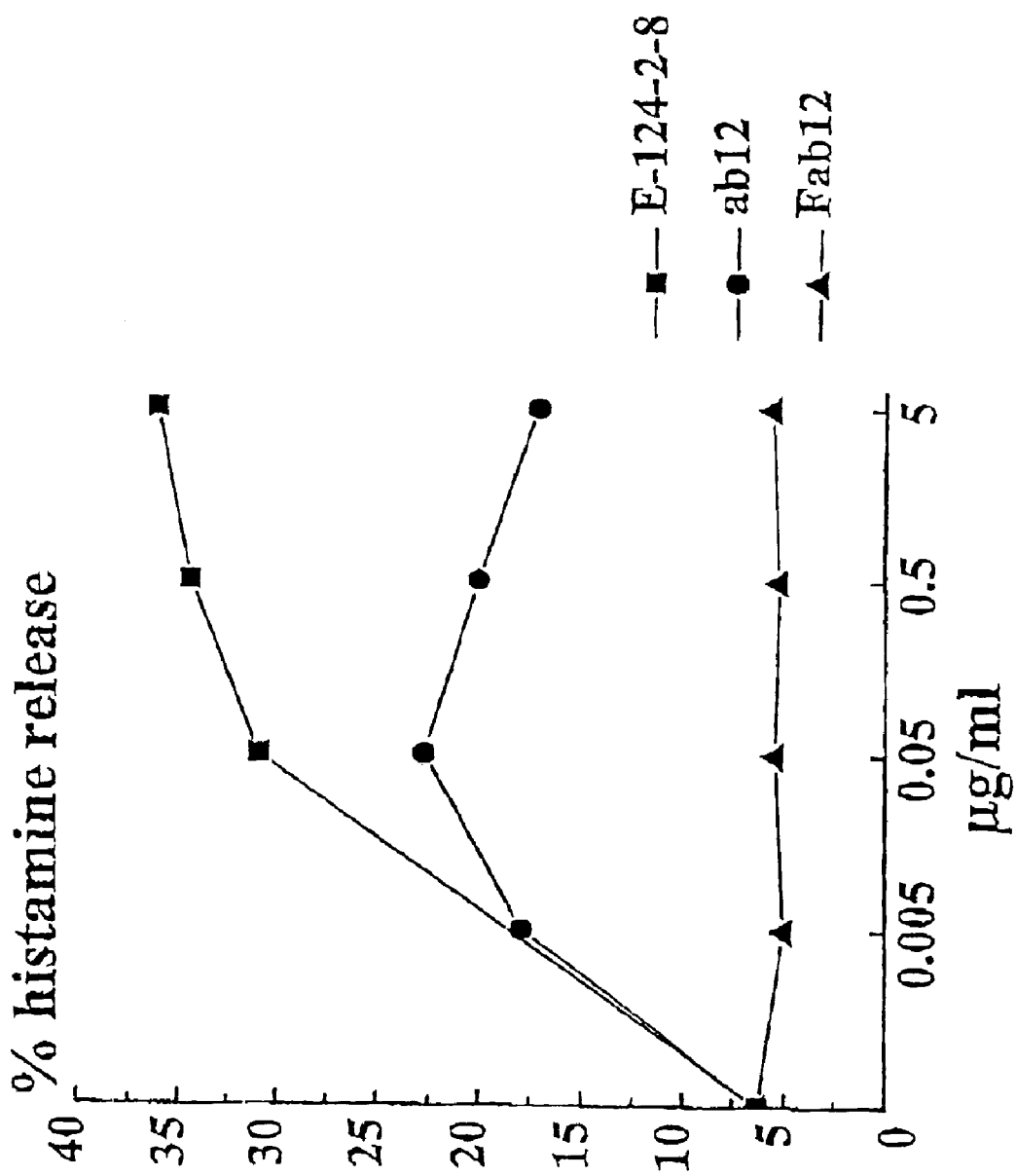

FIG. 3. Fab12 lacks anaphylactic activity. Human basophils were incubated with increasing concentrations of monoclonal anti-human IgE antibodies (E-124-2-8/Dε2, ab 12) and Fab 12 (x-axis). The percentages of released histamine in comparison with total histamine are shown on the y-axis. Results represent means of duplicate determinations.

Figure 4:
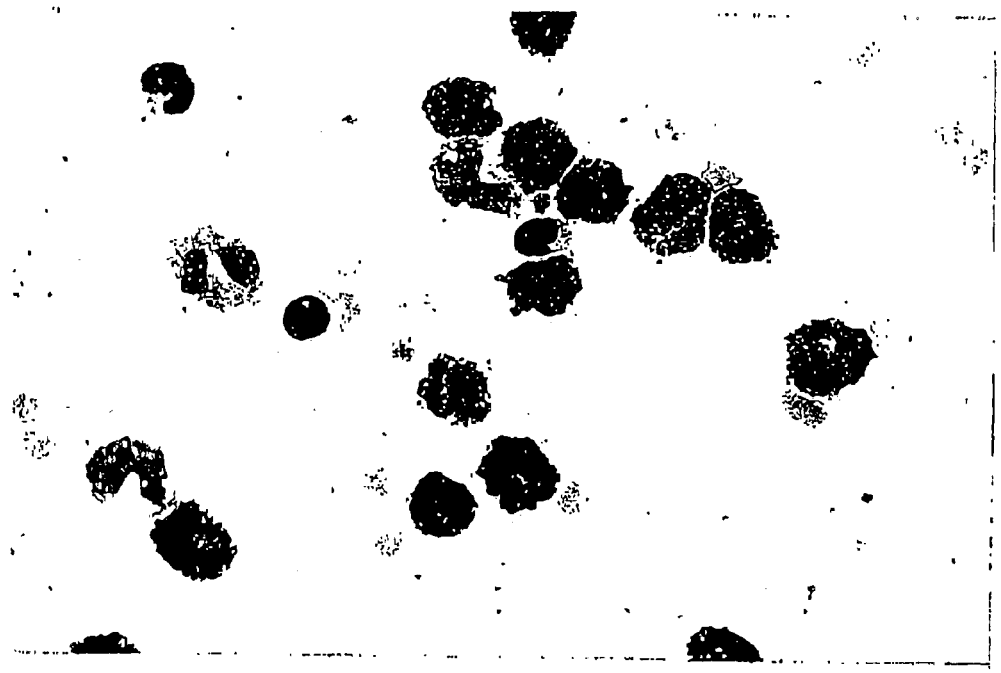
Figure 5:
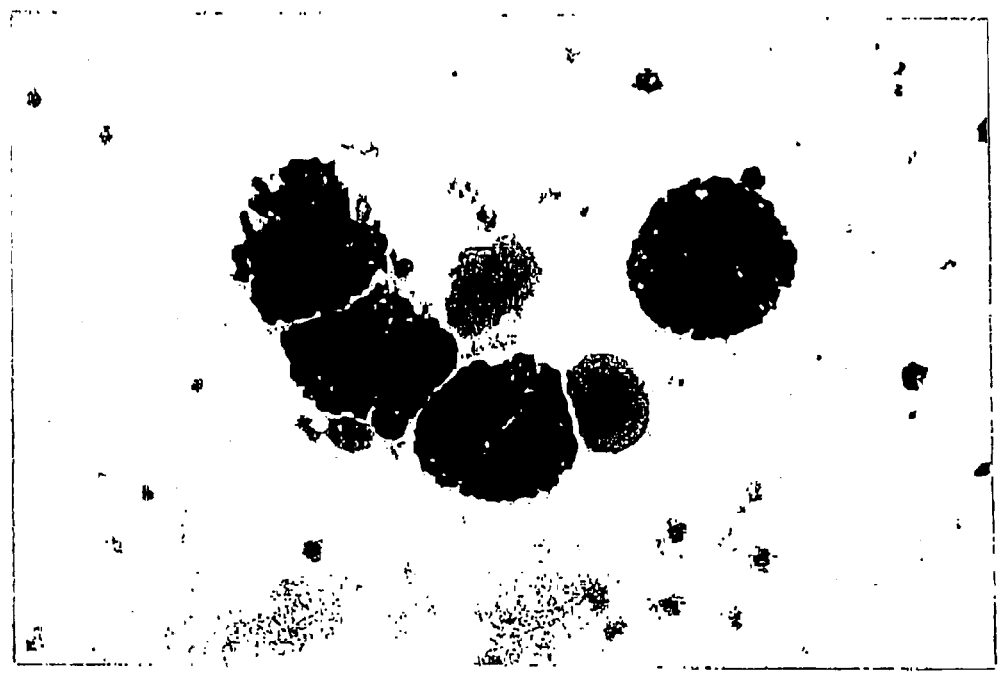

FIGS 4–5. Giesma stained cytospin sample of cells purified from the blood of an atopic patient using antibody 12. FIG. 4 gives an overview of a representative cell preparation whereas FIG. 5 shows a close up of purified basophils.

EXPERIMENTAL SECTION

I. Generation and Characterization of the Chimeric Bet v 1-Specific IgE Antibody, Bip 1

In order to establish a molecular in vitro model for the interaction of a major allergen, its corresponding IgE, and FcεRI, we have constructed a chimeric monoclonal IgE antibody, Bip 1, with specificity for the major birch pollen allergen, Bet v 1 [28, 29].

Messenger RNA was isolated from Bip 1 hybridoma cells [29] by use of Quick Prep Micro mRNA purification kit (Amersham Pharmacia Biotech, Uppsala, Sweden). The variable immunoglobulin heavy chain region (VH) was specifically amplified by use of the Recombinant Phase Antibody System: Mouse ScFv Module (Amersham Pharmacia Biotech, Uppsala, Sweden). The human VH-4 leader sequence (L) was amplified by PCR and subsequently fused to the Bip 1 VH region by use of PCR, Sequence determination of the LVH fragment was performed on an Automated Laser Fluorescent DNA Sequencer (Amersham Pharmacia Biotech, Uppsala, Sweden) using the Auto Read Sequencing Kit (Amersham, Pharmacia, Biotech, Uppsala, Sweden). The LVH fragment was subcloned into the Cla I/Spe I sites of an ε-expression plasmid which contains the genomic region coding for the secreted form of human IgE under the control of Ig promotor and enhancer regions. The construct was introduced into the Bip 1 hybridoma cell line by electroporation (Gene Pulser, Biorad). Stable transfectants were selected by use of geneticin in the culture media. Fusion to SP2/0 cells was performed by use of PEG, Clones producing only IgE were identified by ELISA and subcloned to generate monoclonal cell lines. Out of three different clones secreting chimeric Bip 1 IgE, clone 859 was selected due to superior expression (11 $\mu$g/ml) of chimeric IgE. Specific and total IgE was tested, on supernatant of clone 859 grown in serum free media, in both the Pharmacia CAP System and the Uni CAP System (Pharmacia & Upjohn Diagnostics, Uppsala, Sweden).

An affinity column was prepared by coupling 5 mg rBet v 1 to an AminoLink column (Pierce, Rockford, Ill.). Cell culture supernatant (100 ml/run) containing chimeric Bip 1 IgE antibodies (2600 kU/1 IgE) were applied to the Bet v 1 affinity column. The column was washed with PBS, and bound chimeric Bip 1 IgE was eluted with 5 M $MgCl_2$. The Bip 1 IgE-containing eluent was dialyzed against PBS at 4° C. and lyophilized. Approximately 90 $\mu$g chimeric Bip 1 IgE antibody could be purified. Purified lyophilized chimeric IgE was dissolved in phosphate buffered saline. Purity, concentration and quality of chimeric Bip 1 IgE were analyzed by non-reducing SDS-PAGE and Coomassie Brilliant Blue (Imperial Chemical Industries, Ltd., Macclesfield, U.K.) staining of the gels as well as by exposure of nitrocellulose-blotted chimeric Bip 1 IgE to anti-human IgE antibodies. Chimeric Bip 1 migrated as a single band of 190 kDa with no signs of degradation and reacted with anti-human IgE antibodies (data not shown).

II. Recombinant Proteins and $^{125}$I-Labeling of Purified Proteins

Recombinant birch pollen allergen, rBet v 1 [28] was expressed in *E. coli* and purified as described [30]. Recombinant baculovirus-expressed alpha chain of human FcεRI was purified [17]. Comparable amounts (30 $\mu$g) of purified proteins were $^{125}$I-labeled using the chloramine-T method and purified via a Sephadex PD10 column (Pharmacia). The specific activities of the radiolabeled proteins were determined by $\gamma$-counting of equal aliquots in a $\gamma$-counter (Wallach, Turku, Finland).

III. Anti-IgE Antibodies and Fragments thereof $^{125}$I-labeled anti-human IgE antibodies (RAST) were purchased from Pharmacia & Upjohn (Uppsala, Sweden). The mouse monoclonal $IgG_1$ anti-birch profilin antibody, 4A6 is described [31]. A panel of 25 mouse monoclonal anti-human IgE antibodies was raised by immunization of Balb/c mice with 0.5 ml intra peritoneal injections of purified IgE (ND) Fc. The first injection 75 $\mu$g was given in CFA (Complete Freud's Adjuvans) followed by 50 $\mu$g booster injections on day 30, 33 and 34 in physiological saline. Hybridomas were produced by fusion with the SP2/0 cell line partner. Cloning of the hybridomas was done by limiting dilution. Medium from wells with single cell origin as determined by ocular inspection was tested in ELISA using a polystyrene 96 well format with passively adsorbed IgE (ND). Affinity-purified rabbit anti-mouse IgG (Fc) was used as detecting antibody. Clonality and mouse $IgG_1$ isotype was determined by isoelectric focusing, Phast System (Pharmacia Biotech, Uppsala, Sweden) and BIAcore measurements (Biacore, Uppsala, Sweden). mAb 12 was produced in roller bottles in DMEM in serum free media. The resulting mAb 12 containing 0.45 $\mu$m-filtered medium (Millipore, Molsheim, France) was purified using FPLC System over a 10 cm XK50 protein A Sepharose 4FF column (Pharmacia Biotech, Uppsala, Sweden) with a linear flow rate of 30 cm/h and eluted with 0.1 M citrate buffer pH=5.0. The resulting mAb containing peak was neutralised by 1.0 M NaOH and concentrated in an Amicon ultrafiltration cell with a PM 30 filter to a final concentration of 5 mg/ml followed by size exclusion chromatography on a 100 cm, XK50 Superdex 200 pg column (Pharmacia Biotech, Uppsala, Sweden) equilibrated it 0.02 M phosphate buffered saline, pH=7.4. Purity was determined to exceed 95% according to SDS-PAGE, Phast System (Pharmacia Biotech, Uppsala, Sweden). Fab12 was produced from purified mAb12 by papain digestion using an ImmunoPure Fab preparation kit (Pierce, Rockford, Ill.). The purity and molecular weight of the Fab12 preparation was checked by SDS-PAGE.

IV. Screening for Anti-IgE Antibodies

Screening for monoclonal anti-human IgE antibodies that can inhibit the interaction of chimeric Bip 1 and alpha chain was performed by overlay competition experiments. A panel of 25 mouse monoclonal anti-human IgE antibodies and, for control purposes, an isotype matched monoclonal antibody, 4A6 [31], without specificity for human IgE, purified recombinant alpha, chain or buffer alone were tested for their capacity to inhibit binding of chimeric Bip 1 IgE to nitrocellulose-bound alpha chain, Chimeric Bip 1 IgE was preabsorbed with 50 $\mu$g/ml of anti-human IgE antibodies and control reagents for 4 hours at 4° C. and was then exposed to nitrocellulose-dotted recombinant alpha chain at 4° C. overnight. Membranes were washed and bound chimeric Bip 1 IgE was detected with $^{125}$I-labeled rBet v 1 by overnight incubation at room temperature.

One of the blocking antibodies obtained, mAb 12, as well as mAb 12-derived Fab fragments exhibited the unique property to strongly inhibit the IgE-FcεRI interaction and to recognize $\alpha$-chain—as well as basophil-bound IgE antibodies.

V. Immunoelectron Microscopy

Immunoelectron microscopic analysis of monoclonal antibodies and immune complexes were performed by negative staining as previously described [32, 33]. IgE was viewed alone and in complex with whole or mAb 12 F(ab')$_2$ fragments. mAb 12 was digested with pepsin-agarose (Pierce) overnight at 37° C. according to the manufacturers instructions. The F(ab')$_2$ fraction was separated from other digestion products by HPLC. Reactants (at ~1 mg/ml each) were mixed in borate buffered saline and incubated at room temperature for 30 minutes. Following incubation, the reactants were allowed to bind to carbon membranes, stained with uranyl formate, and mounted on copper grids for analysis. Electron micrographs were recorded at 100,000 fold magnification on a JEOL CX 1200 electron microscope.

Many of the uncomplexed IgE molecules did not display the clear three armed "Y"-shaped configuration typical of other monomeric Ig forms (FIG. 1a). This is consistent with a recent report in which the Fc of Fab-tagged IgE showed similar configurations [34]. When mixed with whole mAb 12, a variety of small complexes, chains and rings were observed but were uninterpretable due to the difficulty in distinguishing between the IgG probe and the IgE target molecules (data not shown. Consequently, we digested mAb 12 with pepsin to yield F(ab')$_2$ fragments. When IgE was mixed with a molar excess of F(ab')$_2$, the majority of molecules formed cross-shaped figures with two longer pairs of arms at right angles to two or three shorter arms (FIG. 1b). When mixed at molar equivalence, chains and, less frequently, rings of molecules were observed (FIG. 1c). Closer examination revealed that the longer arms are composed of two segments each. We interpret these images as showing two F(ab')$_2$ anti-IgE (the long arms positioned laterally in FIG. 1b and the linking molecules of the chain in FIG. 1c) reacting with epitopes on either side of the Fc of IgE at a position very close to the geometric center of the molecule. Based on previously published models of IgE, this would place the epitopes near the Cε2-3 juncture. Relatively few of the complexes clearly show three putative IgE arms (FIGS. 1b and 1c). Yet most showed one narrower arm (Fc) and what appeared to be a pair of arms (Fabs) in close contact or partially superimposed upon each other as depicted diagrammatically in FIGS. 1b and 1c.

VI. Combined Toluidine Blue/Immunofluorescence Staining of Human Basophils

Binding of monoclonal anti-human IgE antibodies to basophil-bound IgE was analyzed by a double staining technique using toluidine blue and indirect immunofluorescence as described [35]. Mononuclear cells enriched from the peripheral blood of two healthy volunteers were incubated with monoclonal anti-human IgE antibody E-124-2-8/Dε2 (Immunotech, Marseille, France), monoclonal anti-human IgE antibody 12, anti-IL-3Rα(CD 123), monoclonal antibody 9F5 (PharMingen, San Diego, Calif.), and, for control purposes, with anti-human IgM antibody (PharMingen) or buffer alone for 30 min at 4° C. After incubation, mononuclear cells were washed twice in phosphate buffered saline, and then exposed to fluorescein-labeled goat F(ab')$_2$ anti-mouse IgG for 30 min at 4° C. Cells were fixed in 0.025% glutaraldehyde solution for 1 min, and incubated with toluidine blue (0.0125%) for 12 min at room temperature. After washing, cells were analyzed using a fluorescence microscope (Olympus, Vienna).

mAb 12 differs substantially from the previously described anti-human IgE antibodies (e,g., BSW17) [36, 37] as, despite its ability to block the binding of human IgE to FcεRI and its reactivity to the FcεRI-binding region of human IgE, mAb 12 was able to recognize alpha chain—as well as basophil-bound IgE antibodies. The most likely explanation for this is that mAb 12 interact exactly with or very close to the receptor binding site of human IgE and due to the 1:1 stoichiometry of the IgE-FcεRI interaction [38, 39] binds to one of the IgE constant domains whereas the second domain can interact with the alpha chain. This assumption is supported by results obtained via two types of experiments. 1.) mAb 12-derived Fabs despite reacting with receptor-bound IgE and preventing IgE binding to the receptor did not induce histamine release from human basophils and 2.) Negative stain immunoelectron microscopy showed that mAb 12 F(ab')2 bound on either side of the Fc of IgE near the Cε2-3 juncture.

VII. Histamine Release Experiments

Histamine release experiments were performed with peripheral blood polymorphonuclear leukocytes (PMN) from healthy volunteers using anti-human IgE antibodies E-124-2-8/Dε2 (Immunotech, Marseille, France), mAb 12, as well as with Fab 12. PMN were enriched from heparinized blood samples using Dextran T70 [40], washed and resuspended in histamine release buffer (HRB). HRB containing 25 mM Tris (pH=7.6), 5 mM KCl, 130 mM NaCl, and human serum albumin at 0.33 mg/ml was used for the washing of the cells. The same buffer supplemented with 0.6 mM Ca$^{2+}$ and 1 mM Mg$^{2+}$ was used in histamine release experiments. The capacity of anti-human IgE antibodies to induce basophil histamine release by crosslinking of FcεRI-bound IgE antibodies was tested by exposing PMN to various concentrations of anti-human IgE antibodies at 37° C. for 30 min and measurement of liberated histamine as described [40]. The desensitizing effects of anti-human IgE antibodies E-124-2-8/Dε2 and mAB 12 on anti-IgE-induced histamine release were analyzed as follows [41]. Briefly, PMN were first incubated either with i.) HRB containing 0.01 M EDTA, ii.) HRB containing 0.01 M EDTA and E-124-2-8/Dε2(1 μg/ml), iii.) HRB containing 0.01 M EDTA and mAB 12 (1 μg/ml), or iv.) IIRB containing 0.01 M EDTA and an anti-human IgM antibody (1 μg/ml) (PharMingen) for 10 min at 37° C. Then, cells were washed and incubated with various concentrations of E-124-2-8/Dε2 (0.01, 0.1, or 1.0 μg/ml) or mAb 12 (0.01, 0.1, or 1.0 μg/ml) diluted in HRB for 30 min at 37° C. Cells were centrifuged and the cell-free supernatants were recovered. Histamine released in the cell-free supernatants was measured by radioimmunoassay (Immunotech) and has been calculated as percentage of total histamine (cellular plus extracellular).

Figure 2A:
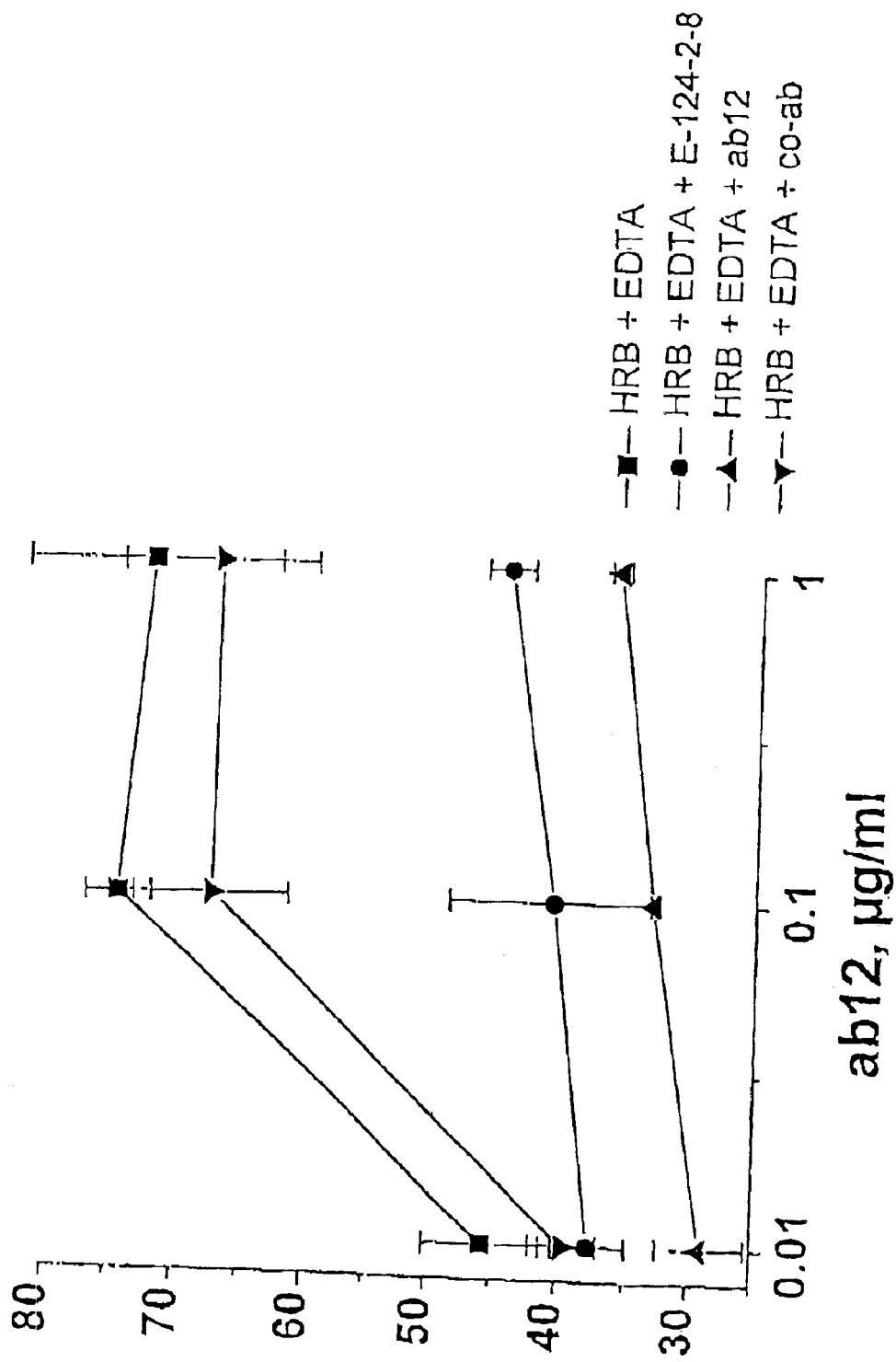
Figure 2B:
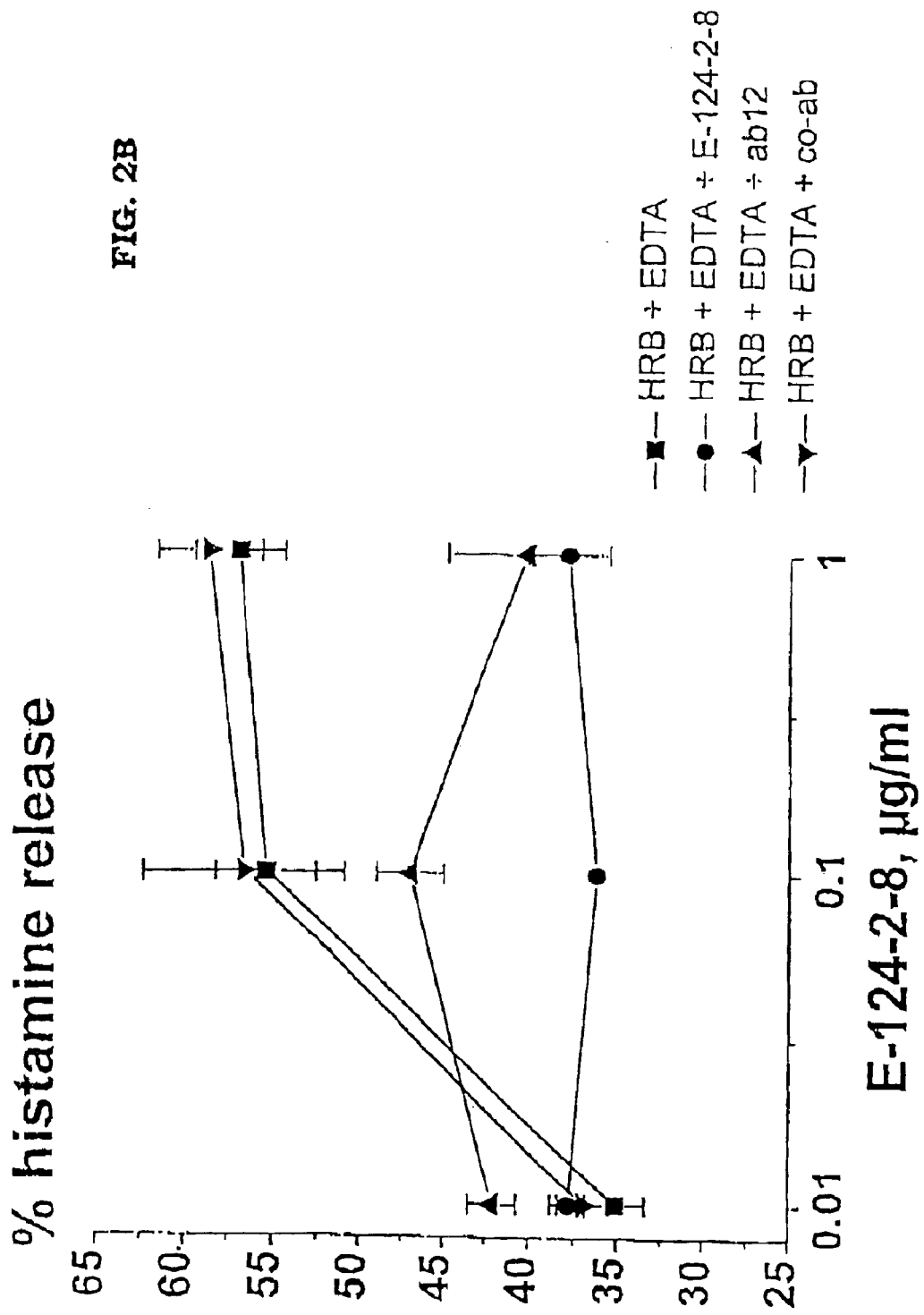

Preincubation of enriched human basophils with mAb 12 or E-124-2-8/Dε2 in EDTA-containing HRB caused desensitization against subsequent IgE-dependent cell activation (FIGS. 2a and 2b). In particular, the subsequent exposure to either mAb 12 or E-124-2-8/Dε2 produced a markedly reduced histamine release response (FIGS. 2a and 2b), when compared to preincubation of human basophils in HRB and EDTA alone, or to HRB and EDTA containing a control anti-human antibody. The possibility that incubation of basophils with anti-human IgE antibodies in HRB containing EDTA has caused release of mediators was excluded by the lack of histamine in the culture supernatants obtained from granulocytes after the preincubation (data not shown).

When we incubated human PMN with increasing concentrations of purified monoclonal anti-human IgE antibodies (mAb 12 or E-124-2-8/Dε2) we found that mAb 12 induced much less (approximately 50% reduced) histamine release than E-124-2-8/Dε2 (FIG. 3). The very same preparation of the mAb 12-derived Fab which had inhibited human IgE binding to alpha chain and which had reacted with alpha chain-bound IgE did not induce any histamine release up to a concentration of 5 μg/ml (FIG. 3).

Fab 12 is a non-anaphylactic competitor of the IgE-FcεRI interaction with a rather low molecular weight. If produced as recombinant Fab fragment containing humanized frame work regions it may be administered to atopic patients such as rhuMAb-E25 to complex and remove circulating IgE [23–25, 42]. Compared with the previously described anti-human IgE antibody (rhuMAb-E25) [23–25, 42], Fab 12 has an as we believe important advantage: In addition to lack of anaphylactic activity, Fab 12 reacts with IgE antibodies which are bound via FcεRI to basophils and thus presumably also to mast cells, eosinophils and antigen-presenting cells containing FcεRI-bound IgE. Fab 12 may therefore not only be used for the depletion of IgE antibodies from the circulation but also to target effector as well as inducer cells of atopy for therapeutical intervention at the cellular level. When used for selective extracorporal plasmapheresis, Fab 12 will deplete IgE antibodies as well as IgE-bearing cells without requiring the administration into patients [43].

VIII. Human Basophils Purified from Heparinized Blood of an Allergic Patient

Isolation of IgE-bearing cells out of whole blood using mAb12 heparinized blood samples from allergic patients and non-atopic individuals were washed one time with PBS, 0.1% BSA and were incubated with mAb 12 (10 μg/ml) or with an isotype-matched control antibody (10 μg/ml) for 30 minutes at room temperature under gentle agitation. Pretreated cells were collected by centrifugation at 800×g for 15 minutes and were washed two times with PBS, 0.1% BSA to remove unbound antibodies. CELLection™ Dynabeads (Dynal, Hamburg, Germany) containing a human anti-mouse IgG attached via a DNA linker were washed according to the manufacturers instruction and were incubated with the pretreated cells for 30 minutes at 4° C. by end over end rotation. The ratio of beads to target cells was at least 5:1. Target cells were attached to the tube wall by the Dynal Magnetic Particle Concentrator (Dynal) and the supernatant was discarded. Rosetted cells wore washed two times with PBS, 0,1% BSA. After the last wash, rosetted cells were gently resuspended in RPMI 1640 medium with HEPES and L-Glutamine (Gibco BRL) and 1% FCS pre-warmed to 37° C. Beads were removed from cells by adding releasing buffer, containing DNAse, (Dynal) for 20 minutes at room temperature. After determination of the cell count in the sample, the identity of isolated cells was determined by Giemsa staining of cytospin preparations. Result: Antibody 12 can be used for single, step purification of human basophils. To study whether antibody 12 can be used for the depletion of IgE-bearing cells, heparinized blood samples from atopic patients were incubated with antibody 12 and Dynabeads containing human anti-mouse IgG. As exemplified in FIG. 4, more than 80% pure basophils could be isolated a single step purification procedure directly from the blood of atopic patient. In addition to basophils, a small percentage other IgE-bearing cells (monocytes, lymphocytes: FIG. 4, and eosinophils; data not shown) were copurified. The close up in FIG. 5 shows purified basophils.

IX. Reduction of IgE Level in Patient Serum

Patient A had a total serum IgE level of 12620 kU/L and patient B 1614 kU/L as determined by CAP-measurements. 50 ml of each sersum was applied to an affinity column which contained 10 ml gel volume of antibody 12 bound to CnBr activated Sepharose 4B. In the case of patient A, the total serum IgE was reduced to 272 kU/L and in the case of patient B to 12 kU/L after application of serum to the column. Total IgE measurements wee results of duplicate determinations. These results show that antibody 12 can be sued to deplete more than 95% of IgE from serum/plasma of allergic patients with high IgE levels.

REFERENCES

1 Kay, A. B., *Allergy and Allergic Diseases*, Blackwell Science Ltd., Oxford, U.K. 1997.
2 Casolaro, V., Georas, S. N., Song, Z. and Ono, S. J., Biology and genetics of atopic disease. *Curr. Opin. Immunol.* 1996, 8: 796–803.
3 Beaven, M. A. and Metzger, H., Signal transduction by Fc receptors: the Fc epsilon RI case. *Immunol. Today* 1993, 14: 222–226.
4 Mudde, G. C., Van Reijsen, F. C., Boland, G, J., de Gast, G. C., Bruijnzeel, P. L. and Bruijnzeel Koomen, C. A., Allergen presentation by epidermal Langerhans cells from patients with atopic dermatitis is mediated by IgE *Immunology* 1990. 69: 335–341.
5 Maurer, D., Ebner, C., Reininger, B., Fiebiger, E., Kraft, D., Rinet, J. P. and Stingl, G., The high affinity receptor (RcεRI) mediates IgE-dependent allergen presentation, *J. Immunol.* 1995. 154: 6285–6290.
6 Bieber, T., FcεRI on antigen-presenting cells, *Curr. Opin. Immunol.* 1996, 8: 773–777.
7 Ishizaka, K. and Ishizka, T., Identification of gamma-E antibodies as a carrier of reagenic activity. *J. Immunol.* 1967. 99: 1187–1198.
8 Johannson, S. G. O. and Bennich, H., Immunological studies of an atypical (myeloma) immunoglobulin, *Immunology* 1967. 13: 381–394.
9 Ravetch, J. V. and Kinet, J. P., Fc receptors. *Ann. Rev. Immunol.* 1991. 9: 7–492.
10 Helm, B., Spivey, A. C. and Padlan, E. A., Peptide blocking of IgE/receptor interaction: possibilities and pitfalls. *Allergy* 1997. 52: 1155–1169.
11 Helm, B., Marsh, P., Vercelli, D., Padlan, B., Gould, H. and Geha, R., The mast cell binding site on human immunoglobulin E. *Nature* 1988. 331: 180–183.
12 Helm, B., Sayers, I., Higginbottom, A., Cantarelli Machado, D., Ling, Y., Ahmad, K., Padlan, E. A. and Wilson, A. P. M., Identification of the high affinity receptor binding region in human immunoglobulin E. *J. Biol. Chem.* 1996. 271: 7494–7500.
13 Nissim, A., Jouvin, M. H. and Eshar, Z., Mapping of the high affinity Fcε receptor binding site to the third constant region domain of IgE. *EMBO J.* 1991. 10: 101–107.
14 Presta, L., Shields, R., O'Conell, L., Lahr, S., Porter, J., Gorman, C. and Jardieu, P., The binding site on human immunoglobulin E for its high affinity receptor. *J. Biol. Chem.* 1994. 269: 26368–26373.
15 Helm, B., Kebo, D., Vercelli, D., Glovsky, M. M., Gould, H., Ishizaka, K., Geha, R. and Ishizaka, T. Blocking of passive sensitization of human mast cells and basophil granulocytes with IgE antibodies by a recombinant human □-chain fragment of 76 amino acids, *Proc. Natl. Acad. Sci. USA* 1989, 86, 9465–9469.
16 Basu, M., Hakimi, J., Dharm, E., Kondas, J. A., Tsien, W. H., Pilson, R. S., Lin, P., Gilfillan, A., Haring, P., Braswell, E. H., Nettleton, M. Y. and Kochan, J. P., Purification and characterization of human recombinant IgE-Fc fragments that bind to the human high affinity IgE receptor. *J. Biol. Chem.* 1993. 268; 13118–13127.
17 Vangelista, L., Laffer, S., Turek, Grönlund, H., Sperr, W. R., Valent, P., Pastore, A. and Valenta, R., The Ig-like modules Cε3 and α2 are the minimal units necessary for human IgE-FcεRI interaction. *J. Clin. Invest.* 1999. 103; 1571–1578.
18 Hamburger, R. N., Peptide inhibition of the Prausnitz-Küstner reaction. *Science.* 1975. 189: 389–390.
19 McDonnell, J. M., Beavil, A. J., Mackay, G. A., Jameson, B. A., Korngold, R., Gould, H. J. and Sutton, B. J., Structure based design and characterization of peptides that inhibit IgE binding to its high-affinity receptor. *Nat. Struct. Biol.* 1996, 3: 419–426.
20 Garman, S. C., Kinet, J. P., and Jardetzky, T. S., Crystal structure of the human high-affinity IgE receptor. *Cell* 1998. 96: 951–961.
21 Hellman, L., Profound reduction in allergen sensitivity following treatment with a novel allergy vaccine, *Eur. J. Inmunol.* 1994. 24, 415–420.
22 Wiegand, T. W., Williams, P. B., Dreskin, S. C., Jouvin, M. H., Kinet, J. P. and Tasset, D., High-affinity oligonucleotide ligands to human IgE inhibit binding to Fc epsilon receptor I. *J. Immunol.* 1996. 157: 221–230.
23 Presta, L. G., Lahr, S. J., Shields, R. L., Porter, J. P., Gorman, C. M., Fendly, B. M. and Jardieu, P., Humanization of antibody directed against IgE. *J Immunol.* 1993. 151: 2623–2632.
24 Heusser, C. and Jardieu, P., Therapeutic potential of anti-IgE antibodies. *Curr. Opin. Immunol.* 1997. 9: 805–813.
25 Holgate, S. T., Corne J., Jardieu P., Fick, R. B. and Heusser, C. H., Treatment of allergic airways disease with anti-IgE. *Allergy* 1998, 53; 83–88.
26 Fei, D. T., Lowe, J. and Jardieu, P., A novel bioactivity assay for monoclonal antibodies directed against IgE. *J. Immunol. Methods* 1994, 171: 189–199.
27 Heusser, C. H., Wagner, R., Bews J. P. A., Coyle, A., Bertrand, C., Einsle, K., Kips, J., Eum, S. Y., Lefort, J. and Vargafting, B. B., Demonstration of the therapeutic potential of non-anaphylactogenic anti-IgE antibodies in murine models of skin reaction, lung function and inflammation. *Int. Arch. Allergy Immunol* 1997, 113: 231–235.

28 Breiteneder, H., Pettenburger, K., Bito, A., Valenta, R., Kraft, D., Rumpold, H., Scheiner, O. and Breitenbach, M., The gene coding for the major birch pollen allergen Bet v I, is highly homologous to a pea disease resistance response gene. *EMBO J.* 1989. 8: 1935–1938.

29 Laffer, S., Vangelista, L., Steinberger, P., Kraft, D., Pastore, A. and Valenta, R., Molecular characterization of Bip 1, a monoclonal antibody that modulates IgE binding to birch pollen allergen, Bet v 1. *J. Immunol.* 1996. 157: 4953–4962.

30 Hoffmann-Sommergruber, K., M., Susani, M., Ferreira, F., Jertschin, P., Ahorn, H., Steiner, R., Kraft, D., Scheiner, O. and Breiteneder, H., High-level expression and purification of the major birch pollen allergen, Bet v 1. *Protein Expr. Purif.* 1997. 9: 33–39.

31 Wiedemann, P., Giehl, K., Almo, S., Fedorov, A. A., Girvin, M., Steinberger, P., Rüdiger, M., Ortner, M., Sippl, M., Dolecek, D., Kraft, D., Jockusch, B. and Valenta, R., Molecular and structural analysis of a continuous birch protein epitope defined by a monoclonal antibody. *J. Biol. Chem.* 1996. 271: 29915–29921.

32 Roux, K. H., Immunoelectron microscopy of idiotype-anti-idiotype complexes. *Meth. Enzymol.* 1989. 178: 130–144.

33 Roux, K. H., Negative stain immunoelectron microscopic analysis of small macromolecules of immunologic significance, *Methods* 1996. 10: 247–256.

34 Roux, K. H., Strelets, L., Brekke, O. H., Sandlie, I. and Michaelsen, T. E., Comparison of the ability of human IgG$_3$ hinge mutants, IgM, IgE, and IgA2, to form small immune complexes: A role for flexibility and geometry. *J. Immunol.* 1998. 161: 4083–4090.

35 Valent, P., Asham, L. K., Hinterberger, W., Eckersberger, P., Majdic, O., Lechner, K., Maurer, D. and Bettelheim P., Mast cell typing: Demonstration of a distinct hemopoletic cell type and evidence for immunophenotypic relationship to mononuclear phagocytes. *Blood* 1989. 73: 1778–1785.

36 de Weck, A. L. and Stadler, B., Good or bad IgE and anti-IgE antibodies: new molecular concepts. In: Kraft, D., and Sehon, A, editors. *Molecular biology and immunology of allergens.* Boca Raton, Fla.; CRC Press 1993, pp 101–112.

37 Rudolf, M. P., Furukawa, K., Miescher, S., Vogel, M., Kricek, F. and Stadler, B. M., Effect of anti-IgE antibodies on FcεRI-bound IgE. *J. Immunol.* 1996. 157: 5646–5652.

38 Keown, M. B., Ghirlando, R., Young, R. J., Beavil, A. J., Owens, R. J., Perkins, S. J., Sutton, B. J. and Gould, H. J., Hydrodymanic studies of a complex between the Fc fragment of human IgE and a soluble fragment of the Fc epsilon RI alpha chain. *Proc. Natl. Acad. Sci. USA* 1995. 92: 1841–1845.

39 Keown, M. B., Ghirlando, R., Mackay, G. A., Sutton, B. J. and Gould, H. J., Basis of the 1:1 stoichiometry of the high affinity receptor Fc epsilon RI-IgE complex. *Eur. Biophys. J.* 1997. 25: 471–476.

40 Valent, P., Besemer, J., Muhm, M., Majdic, O., Lechner, K. and Bettelheim, P., Interleukin-3 activates human blood basophils via high affinity binding sites. *Proc. Natl. Acad. Sci. USA* 1989. 86: 5542–5546.

41 Valenta, R., Sperr, W. R., Ferreira, Valent, P., Sillaber, C., Tejkl, M., Duchene, M., Ebner, C., Lechner, K., Kraft, D. and Scheiner, O., Induction of specific histamine release from basophils with purified natural and recombinant birch pollen allergens. *J. Allergy Clin. Immunol.* 1993. 91: 88–97.

42 Milgrom, H., Fick, R. B., Su, J. Q., Reimann, J. D., Bush, R. K., Watrous, M. L. and Metzger, W. J., Treatment of allergic asthma with monoclonal anti-IgE antibody. *N. Engl. J. Med.* 1999, 341: 1966–1973.

43 Lebedin, Y. S, Gorchakov, V. D., Petrova, E. N., Kobylansky, A. G., Raudla, L. A., Tatarsky, A. R., Bobkov, E. V., Adamova, I. Y, Vasilov, P. G. and Nasanov, E. L., Ex vivo removal of IgE in atopic asthma by extracorporal plasmoimmunoadsorption (EPIA): development of a clinical adsorbent, *Int. J. Artif. Organs* 1991. 14: 508–514.

What is claimed is:

1. An anti-IgE Fab fragment from the antibody produced by the hybridoma cell line deposited at the European Collection of Cell Cultures under accession no. 02032734, having the following characteristics:

a) inhibits the IgE-FcεRI interaction;

b) binds to free and cell-bound IgE; and c) is non-anaphylactic.

2. The Fab according to claim 1 which is synthetically or recombinantly produced.

3. A recombinant anti-IgE Fab fragment in which the framework regions of the Fab fragment from the antibody produced by the hybridoma cell line deposited at the European Collection of Cell Cultures under accession no. 02032734, are humanized.

4. A method for the treatment of an atopic condition, comprising administering to a patient in need thereof an effective amount of the anti-IgE Fab of claim 1.

5. A method for the treatment of an atopic condition, comprising administering to a patient in need thereof an effective amount of the anti-IgE Fab of claim 2.

6. A method for the treatment of an atopic condition, comprising administering to a patient in need thereof an effective amount of the anti-IgE Fab of claim 3.

7. The method of claim 4, wherein said atopic condition is an acute atopic condition.

8. The method according to claim 4, wherein said atopic condition is a chronic atopic condition.

9. The method according to claim 4, wherein said anti-IgE Fab is further characterized by a capability of depleting IgE and IgE bearing cells from circulation.

10. The method according to claim 9, wherein said administration is to the patient's blood or blood plasma.

11. The method according to claim 10, wherein said administration is made to the patient's blood or blood plasma outside the patient's body.

12. The method according to claim 6, wherein said anti-IgE Fab is further characterized by a capability of depleting IgE and IgE bearing cells from circulation.

13. The method according to claim 12, wherein said administration is made to the patient's blood or blood plasma outside the patient's body.

14. The method according to claim 5, wherein said administration is to the patient's blood or blood plasma.

15. The method according to claim 14, wherein said administration is made to the patient's blood or blood plasma outside the patient's body.

* * * * *